US012636179B2

(12) United States Patent
Cui et al.

(10) Patent No.: US 12,636,179 B2
(45) Date of Patent: May 26, 2026

(54) DEVICE FOR RAPID REDUCTION AND EXTERNAL FIXATION OF A LIMB FRACTURE BASED ON AUGMENTED REALITY

(71) Applicant: The Fourth Medical Center of the Chinese People's Liberation Army General Hospital, Beijing (CN)

(72) Inventors: Xiang Cui, Beijing (CN); Chi Ma, Beijing (CN); Houchen Lv, Beijing (CN); Yong Xie, Beijing (CN); Licheng Zhang, Beijing (CN); Peifu Tang, Beijing (CN)

(73) Assignee: The Fourth Medical Center of the Chinese People's Liberation Army General Hospital, Beijing (CN)

( * ) Notice: Subject to any disclaimer, the term of this patent is extended or adjusted under 35 U.S.C. 154(b) by 0 days.

(21) Appl. No.: 19/325,653

(22) Filed: Sep. 11, 2025

(65) Prior Publication Data

US 2026/0007537 A1     Jan. 8, 2026

(30) Foreign Application Priority Data

Sep. 13, 2024    (CN) .......................... 202411286818.4

(51) Int. Cl.
 *A61F 5/058*          (2006.01)
(52) U.S. Cl.
 CPC ................................ *A61F 5/05841* (2013.01)
(58) Field of Classification Search
 CPC ............... A61F 5/05841; A61F 5/0585; A61F
5/05858; A61F 5/05866; A61F 5/05875;
A61F 5/04; A61F 5/042; A61F 5/048;
A61F 5/05; A61F 5/0106; A61F 5/0123;
A61F 5/0144; A61F 2005/0172; A61F
2005/0174; A61B 5/6813; A61B 5/6828;
A61B 5/6829; A61B 5/6824
See application file for complete search history.

(56) References Cited

U.S. PATENT DOCUMENTS

| | | | | | |
|---|---|---|---|---|---|
| 1,517,915 | A | * | 12/1924 | Masland | ............... A61F 5/0585 |
| | | | | | 606/54 |
| 2,055,024 | A | * | 9/1936 | Bittner, Jr. | ............. A61B 17/62 |
| | | | | | 606/56 |
| 4,773,405 | A | * | 9/1988 | Reime | ................... A61F 5/0106 |
| | | | | | 602/25 |
| 5,065,770 | A | * | 11/1991 | Palfray | .................. A61B 5/107 |
| | | | | | 600/587 |
| 5,213,094 | A | * | 5/1993 | Bonutti | ................. A61F 5/0123 |
| | | | | | 601/33 |
| 5,458,599 | A | * | 10/1995 | Adobbati | ........... A61B 17/7225 |
| | | | | | 606/56 |
| 9,872,796 | B1 | * | 1/2018 | Karna | ................. A61F 5/05875 |

(Continued)

*Primary Examiner* — Kari K Rodriquez

(57) ABSTRACT

A device for rapid reduction and external fixation of a limb fracture comprises a C-shaped splint, a fixed splint, a reduction arc plate, and a limiting component. The limiting component includes a connecting frame and a connecting arc plate. An outer wall of the connecting frame is provided with a fixed pressing plate, and a bottom of the fixed pressing plate is provided with a positioning clamping plate. A plurality of positioning slots are provided in the connecting frame and the connecting shaft. The positioning clamping plate is fixedly sleeved in the positioning slots.

6 Claims, 9 Drawing Sheets

(56)  References Cited

U.S. PATENT DOCUMENTS

| | | | |
|---|---|---|---|
| 2011/0301610 A1* | 12/2011 | Ali | A61B 17/00 |
| | | | 606/74 |
| 2019/0167095 A1 | 6/2019 | Krueger | |
| 2019/0380785 A1 | 12/2019 | Davies et al. | |
| 2020/0197209 A1* | 6/2020 | Bejarano | A61F 5/0125 |
| 2022/0265355 A1 | 8/2022 | Ferrante et al. | |
| 2023/0414393 A1* | 12/2023 | Xia | A61F 5/0125 |

* cited by examiner

DEVICE FOR RAPID REDUCTION AND EXTERNAL FIXATION OF A LIMB FRACTURE BASED ON AUGMENTED REALITY

CROSS-REFERENCE TO RELATED APPLICATIONS

This application claims priority to Chinese Patent Application No. 202411286818.4 with a filing date of Sep. 13, 2024. The content of the aforementioned application, including any intervening amendments thereto, is incorporated herein by reference.

FIELD

The present disclosure relates to the field of fracture reduction and fixation devices, and more particularly to a device for rapid reduction and external fixation of a limb fracture based on augmented reality.

BACKGROUND

Severe trauma-induced limb fractures often cause early serious complications such as hemorrhagic shock and wound infections due to inadequate fixation during pre-hospital first aid, endangering patient safety and negatively impacting in-hospital treatment outcomes. Pre-hospital treatment of limb fractures requires repositioning the fracture site first, bringing the broken bone segments together, and using external fixation devices to firmly secure the fracture site. This ensures fixation and stability of the fracture, aiding restoration of normal bone structure and function, promoting fracture healing, and reducing complications.

Due to the high mobility of limbs, inadequate immediate fixation and bandaging after a fracture inevitably worsen injuries. Therefore, emergency treatment of fractures is essential before transferring patients, to minimize abnormal movement at the fracture site. During emergency treatment, manual reduction is typically followed by fixation using steel plates or simple splints combined with bandages. However, this method is time-consuming, complex, and unable to quickly stabilize the fracture. Additionally, the steel plates or splints, being flat, do not conform to irregular limb surfaces, creating gaps between the limb and the fixation device. These gaps will lead to soft-tissue compression and potential skin damage. During transport, movement can exacerbate injury severity, potentially causing irreversible damage. Therefore, the present disclosure provides a device for rapid reduction and external fixation of a limb fracture based on augmented reality, addressing the need to prevent soft-tissue compression during transfer.

SUMMARY

The present disclosure provides a device for rapid reduction and external fixation of a limb fracture based on augmented reality, aiming to solve the technical problem that, when existing fracture reduction and fixation devices are used for reducing and fixing fractures during pre-hospital emergency care of limb fractures, they cannot fit the surface of the limb, resulting in gaps between plates or splints and the limb, causing soft-tissue compression and potentially worsening injury during transport, and the injured limb may suffer aggravated injuries due to shaking during transportation, thereby causing irreversible damage to the patient.

To address the above issues, the present disclosure provides the following technical solutions.

A device for rapid reduction and external fixation of a limb fracture based on augmented reality is provided, which includes a C-shaped splint, a fixed splint, a reduction arc plate, and a limiting component. The C-shaped splint includes a first arc plate and a second arc plate, and a sidewall of the first arc plate and the second arc plate is provided with an arc-shaped connecting frame. The fixed splint is connected to the arc-shaped connecting frame, and a sliding seat is slidably connected inside the fixed splint. A bottom of the sliding seat is provided with an adjusting plate. The reduction arc plate includes a reduction splint and a movable splint, the reduction splint is arranged at a bottom of the adjusting plate, and the limiting component is arranged between the reduction splint and the movable splint.

The limiting component includes a connecting frame and a connecting arc plate, the connecting frame is arranged at an end of the reduction splint and movable splint, and the connecting arc plate is arranged at a further end of the reduction splint and movable splint. An end of the connecting arc plate is provided with a connecting shaft, and the connecting shaft is rotatably inserted into the connecting frame. An outer wall of the connecting frame is provided with a fixed pressing plate, and a bottom of the fixed pressing plate is provided with a positioning clamping plate. A plurality of positioning slots is provided in the connecting frame and the connecting shaft, and the positioning clamping plate is fixedly sleeved in the positioning slot.

Optionally, a limiting sliding groove is provided inside the connecting shaft, a limiting sliding rod is provided at a bottom of the positioning clamping plate, and the limiting sliding rod is slidably sleeved in the limiting sliding groove.

Optionally, the fixed splint includes an arc-shaped plate, both ends of the arc-shaped plate are provided with an arc-shaped hook plate. The arc-shaped connecting frame includes an arc-shaped connecting bracket, and the arc-shaped connecting bracket is provided on the sidewall of the first arc plate and the second arc plate. A hook groove matching a shape of the arc-shaped hook plate is formed between the arc-shaped connecting frame and the first arc plate, and the arc-shaped hook plate is fixedly sleeved in the hook groove. An adjustment sliding groove is provided inside the arc-shaped plate, the sliding seat is slidably connected inside the adjustment sliding groove, and a mounting clamp plate is provided at a top of the reduction splint.

Optionally, an outer wall of the arc-shaped connecting frame is provided with a plurality of limiting blocks, a limiting slot is provided inside the arc-shaped hook plate, the limiting block is engaged inside the limiting slot, and an inner wall of the arc-shaped hook plate is provided with a weakening groove.

Optionally, a threaded sleeve is provided inside the sliding seat, an adjusting screw is provided inside the threaded sleeve, and a bottom of the adjusting screw is connected to a top of an adjusting plate. An outer wall of the adjusting plate is provided with a mounting slot, and mounting clamp plate is fixedly sleeved in the mounting slot.

Optionally, an arc-shaped shifting piece is provided at a top of the sliding seat, a plurality of positioning slots is provided inside the adjustment sliding groove, and the arc-shaped shifting piece is fixedly sleeved in the positioning slot.

Optionally, an end of the first arc plate is provided with a connecting plate. An inner wall of the connecting plate is provided with a plurality of inserting blocks. A plurality of inserting slots is provided inside the second arc plate, the inserting block is fixedly sleeved in the inserting slot. A limiting baffle is provided inside the second arc plate, and a sidewall of the limiting baffle is provided with an elastic pressing plate.

Optionally, a further end of the first arc plate is provided with a rotating shaft, and a further end of the second arc plate is provided with a rotating frame, and the rotating shaft is rotatably sleeved in the rotating frame.

Optionally, a plurality of ventilation holes is provided inside the first arc plate and the second arc plate, and an inner wall of the first arc plate and the second arc plate is provided with a plurality of anti-slip elastic pieces.

Optionally, an elastic plate is provided between the reduction splint and the movable splint, an inner wall of the reduction splint and the movable splint is provided with a plurality of anti-slip pads, and the anti-slip pad is made of rubber. Compared with prior art, the present disclosure can at least have the following advantages.

In the above solution, through the reduction arc plate and limiting component, the reduction arc plate can closely fit the curved limb surface, eliminating gaps between the plate and the limb and preventing displacement of the fracture site caused by movement during transport, thereby avoiding secondary injuries. Furthermore, as the reduction arc plate adapts to the limb's contour, under the action of the fixed pressing plate, the positioning clamping plate can securely engage into the positioning slot inside the connecting frame and connecting shaft, locking the angle between the connecting frame and the connecting arc plate. Parameters between the reduction splint and the movable splint can be preset according to specific requirements. During fracture reduction, the fractured site can be quickly reduced by positions of the reduction splint and the movable splint with the preset parameters, and the fractured site can be clamped and fixed.

By providing a fixed pressing plate in the limiting component, the positioning clamping plate can remain firmly engaged in the positioning slot during use, limiting the angle between the connecting arc plate and the connecting frame. The angle between the movable splint and the reduction splint can thus be adjusted as needed, ensuring the movable splint precisely to fit the limb surface based on the reduction and fixation needs, thereby ensuring the requirement of clamping and fixing the fractured site.

BRIEF DESCRIPTION OF DRAWINGS

The accompanying drawings, incorporated herein and constitute a part of the specification, illustrate embodiments of the present disclosure. Together with the specification, these drawings further serve to explain the principles of the present disclosure, enabling those skilled in the art to implement and use the present disclosure.

REFERENCE NUMERAL

Figure 1:
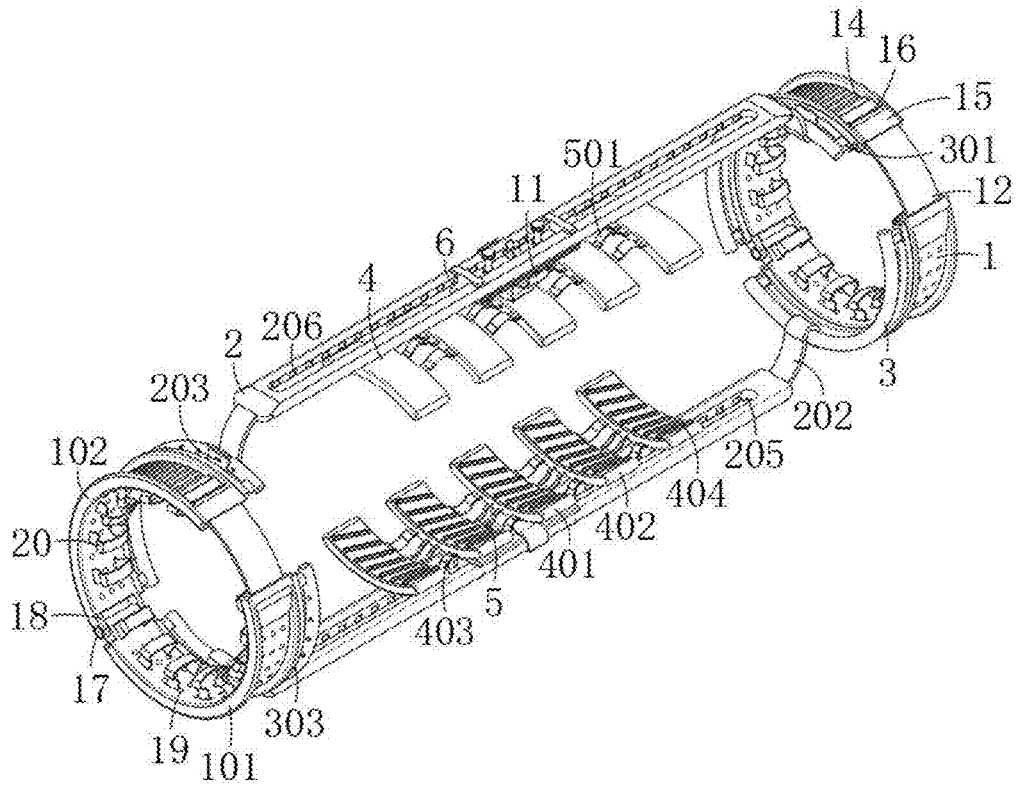
FIG. 1 is a schematic perspective diagram of a device for rapid reduction and external fixation of a limb fracture based on augmented reality.

C-shaped splint 1; first arc plate 101; second arc plate 102; fixed splint 2; arc-shaped plate 201; arc-shaped hook plate 202; limiting slot 203; weakening groove 204; adjustment sliding groove 205; positioning slot 206; arc-shaped connecting frame 3; arc-shaped connecting bracket 301; hook groove 302; limiting block 303; reduction arc plate 4; reduction splint 401; movable splint 402; elastic plate 403; anti-slip pad 404; limiting component 5; connecting frame 501; connecting arc plate 502; connecting shaft 503; fixed pressing plate 504; positioning clamping plate 505; positioning slot 506; limiting sliding rod 507; limiting sliding groove 508; sliding seat 6; adjusting plate 7; arc-shaped shifting piece 8; threaded sleeve 9; adjusting screw 10; mounting clamp plate 11; connecting plate 12; inserting block 13; inserting slot 14; limiting baffle 15; elastic pressing plate 16; rotating shaft 17; rotating frame 18; ventilation hole 19; anti-slip elastic piece 20; mounting slot 21.

As shown in the drawings, specific structures and components are labeled for clearly illustrating the embodiments of the present disclosure. However, this is for illustrative purposes only and is not intended to limit the present disclosure to the specific structures, components, and environments depicted. Those skilled in the art can adjust or modify these components and environments according to practical requirements.

DETAILED DESCRIPTION OF PREFERRED EMBODIMENTS

The following describes in detail a device for rapid reduction and external fixation of a limb fracture based on augmented reality provided by the present disclosure, with reference to the accompanying drawings and specific embodiments. It should be noted that, for clarity and comprehensiveness, the embodiments presented here are preferred examples. Those skilled in the art may also employ other alternative methods to implement the known techniques involved. Moreover, the accompanying drawings are solely intended to provide a clearer description of the embodiments and are not intended to specifically limit the present disclosure.

It should be noted that the references in the specification to "one embodiment", "an embodiment", "example embodiment", or "some embodiments", and the like indicate that the described embodiments may include specific features, structures, or characteristics, but not every embodiment necessarily includes that specific features, structures, or characteristics. Additionally, when describing specific features, structures, or characteristics in association with an embodiment, it should be understood that implementing these features, structures, or characteristics in combination with other embodiments (whether explicitly described or not) is within the knowledge of those skilled in the art.

Generally, terms can be understood, at least in part, from their usage in the context. For instance, depending at least in part on the context, the term "one or more" can be used to describe any single feature, structure, or characteristic, or a combination of multiple features, structures, or characteristics. Similarly, the term "based on" may be understood as not necessarily intended to convey an exclusive set of factors. Instead, depending at least in part on the context, it may allow for the existence of other factors that are not explicitly described.

It is to be understood that the terms used herein such as "on", "above" and "over" shall be interpreted in the broadest manner. Specifically, "on" not only means "directly on" something, but also includes the meaning of being "on" something with intermediate features or layers therebetween; and "above" or "over" not only means being "above" or "over" something, but may also include the meaning of being "above" or "over" something without intermediate features or layers therebetween.

In addition, spatially relative terms such as "below", "under", "lower part", "above", and "upper part" may be used herein for descriptive convenience to describe the relationship between one element or feature and one or more other elements or features, as shown in the accompanying drawings. Spatially relative terms are intended to encompass different orientations of the device in use or operation other than the orientation depicted in the drawings. The device may be oriented in other ways, and the spatially relative descriptors used herein may be interpreted accordingly in a similar manner.

As shown in FIG. 1 to FIG. 9, embodiments of the present disclosure provide a device for rapid reduction and external fixation of a limb fracture based on augmented reality. The device includes a C-shaped splint 1, a fixed splint 2, a reduction arc plate 4, and a limiting component 5. The C-shaped splint 1 includes a first arc plate 101 and a second arc plate 102, a sidewall of the first arc plate and the second arc plate is provided with an arc-shaped connecting frame 3. The fixed splint 2 is connected the arc-shaped connecting frame 3. A sliding seat 6 is slidably connected inside the fixed splint 2, and a bottom of the sliding seat 6 is provided with an adjusting plate 7. The reduction arc plate 4 includes a reduction splint 401 and a movable splint 402, and the reduction splint 401 is arranged at a bottom of the adjusting plate 7.

As illustrated in FIG. 6 to FIG. 9, the limiting component 5 is positioned between the reduction splint 401 and the movable splint 402. The limiting component 5 comprises a connecting frame 501 and a connecting arc plate 502. The connecting frame 501 is arranged at an end of the reduction splint 401 and the movable splint 402, and the connecting arc plate 502 is arranged at a further end of the reduction splint 401 and the movable splint 402. An end of the connecting arc plate 502 is provided with a connecting shaft 503, and the connecting shaft 503 is rotatably inserted into the connecting frame 501. An outer wall of the connecting frame 501 is provided with a fixed pressing plate 504, and a positioning clamping plate 505 is provided at the bottom of the fixed pressing plate 504. A plurality of positioning slots 506 are provided in the connecting frame 501 and the connecting shaft 503, with the positioning clamping plate 505 fixedly sleeved in the positioning slots 506. a limiting sliding groove 508 is provided inside the connecting shaft 503, a limiting sliding rod 507 is provided at a bottom of the positioning clamping plate 505, and the limiting sliding rod 507 is slidably sleeved in the limiting sliding groove 508. Both ends of the reduction splint 401 and movable splint 402 are provided with the connecting frame 501 and connecting arc plate 502, arranged in a cross pattern. Moreover, the connecting frame 501 is rotatably connected to the connecting arc plate 502 via the connecting shaft 503. Both the connecting frame 501 and the connecting arc plate 502 are arc shaped. The fixed pressing plate 504 is an arc-shaped plate, which is made of metal and has a certain degree of elasticity. The connecting frame 501 is rotatably connected to the connecting arc plate 502 through the connecting shaft 503. Under the action of the elastic plate 403, the movable splint 402 contacts and conforms closely to the limb surface, ensuring tight fitting of the movable splint 402 and reduction splint 401 against the limb, thus preventing gaps between the reduction arc plate 4 and limb, thereby avoiding secondary trauma to the fracture site caused by movement during transport. Additionally, under the action of the fixed pressing plate 504, the positioning clamping plate 505 engages firmly with the positioning slot 506 inside the connecting frame 501 and connecting shaft 503, locking the angle between the connecting frame 501 and connecting arc plate 502. This design allows the parameter between the reduction splint 401 and movable splint 402 to be preset according to usage requirements. During the use of the device, the fractured site can be quickly reduced by using the reduction splint 401 and the movable splint 402 with the preset parameters, and the fractured site can be clamped and fixed, facilitating the use of the device.

Figure 4:
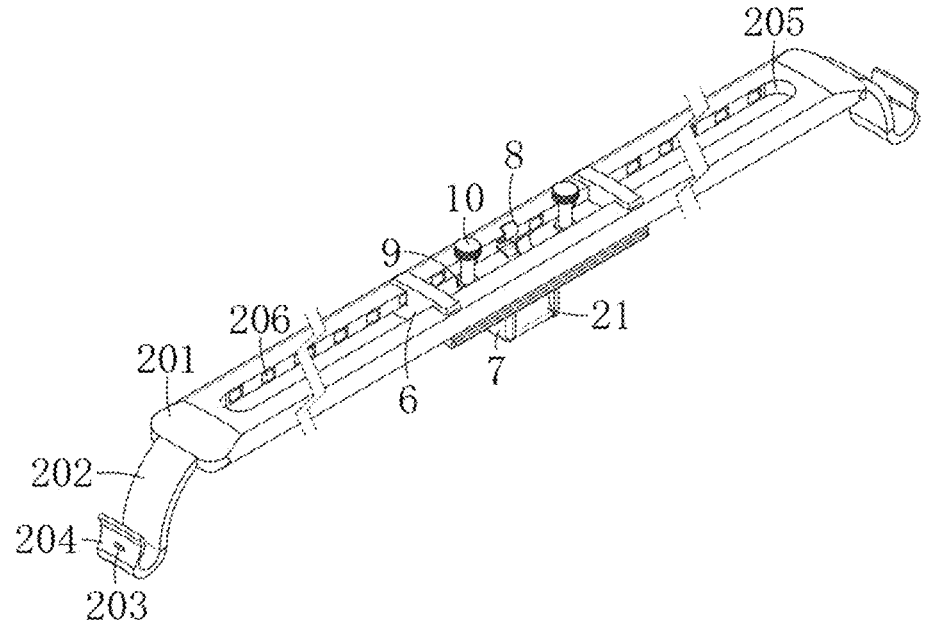
FIG. 4 is a schematic diagram of an enlarged three-dimensional structure illustrating a matching between a connecting component and an adjustment component.

As shown in FIG. 1 and FIG. 4, the fixed splint 2 includes an arc-shaped plate 201, and both ends of the arc-shaped plate 201 are provided with an arc-shaped hook plate 202. The arc-shaped connecting frame 3 includes an arc-shaped connecting bracket 301, provided on the sidewall of the first arc plate 101 and the second arc plate 102. A hook groove 302 matching the shape of the arc-shaped hook plate 202 is formed between the arc-shaped connecting frame 301 and the first arc plate 101. The arc-shaped hook plate 202 is fixedly sleeved in the hook groove 302. An outer wall of the arc-shaped connecting frame 301 is provided with a plurality of limiting blocks 303, and a limiting slot 203 is provided inside the arc-shaped hook plate 202. The limiting block 303 is engaged inside the limiting slot 203. An inner wall of the arc-shaped hook plate 202 is provided with a weakening groove 204. The fixed splint 2 is primarily composed of the arc-shaped hook plate 202 at both ends and the arc-shaped hook plate 202 directly connected to the arc-shaped plate 201. The arc-shaped plate 201 is an arc-shaped plate material with a hollowed-out middle and a certain degree of strength. The fixed splint 2 is suspended within the hook groove 302 on the arc-shaped connecting frame 301 via the arc-shaped hook plate 202. Since the shapes of the hook groove 302 and the arc-shaped hook plate 202 are mutually adapted, once the arc-shaped hook plate 202 and the hook groove 302 are engaged, the fixed splint 2 is installed on the arc-shaped connecting frame 301. This mounting method greatly enhances the mounting efficiency of the reduction arc plate 4. Due to the integral structure of the fixed splint 2, the mounting and transportation are labor-saving and efficient. Furthermore, since the fixed splint 2 is engaged with the arc-shaped connecting frame 3 via the arc-shaped hook plate 202, the fixed splint 2 can slide freely along the arc-shaped connecting frame 301 after assembly. This allows medical personnel to adjust the position of the fixed splint 2 according to the injury location, creating more operational space for cleaning, disinfecting, and subsequent bandaging.

Additionally, a limiting slot 203 is provided inside the arc-shaped hook plate 202. When engaging the arc-shaped hook plate 202 inside the hook groove 302, the limiting block 303 arranged on the outer wall of arc-shaped connecting frame 301 may fit securely into the limiting slot 203. This can limit the position of the fixed splint 2, and effectively locks it in place after adjustment. When repositioning the fixed splint 2, the arc-shaped hook plate 202 can be flexed at the weakening groove 204, disengaging the limiting block 303 from the limiting slot 203, enabling the fixed splint 2 to slide freely on the arc-shaped connecting frame 301, thereby allowing medical staff to adjust the position of the fixed splint 2 according to the location of the affected area.

Figure 5:
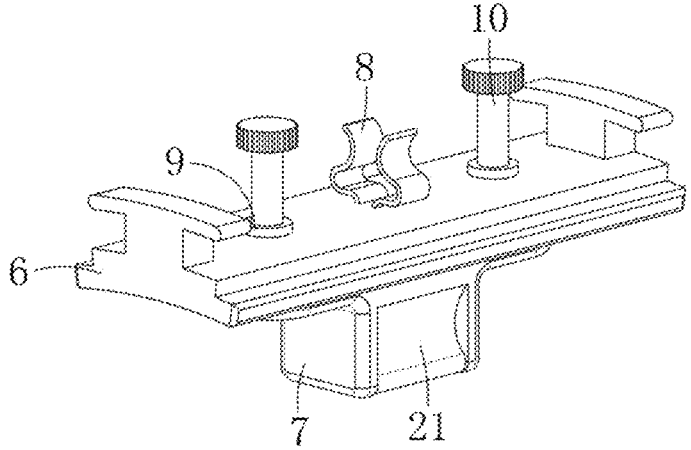
FIG. 5 is a schematic diagram of an enlarged three-dimensional structure of an adjustment component.

As shown in FIG. 4 and FIG. 5, an adjustment sliding groove 205 is provided inside the arc-shaped plate 201, a sliding seat 6 is slidably connected inside the adjustment sliding groove 205. A threaded sleeve 9 is provided inside the sliding seat 6, and an adjustment screw 10 is provided inside the threaded sleeve 9. A bottom of the adjusting screw 10 is connected to a top of an adjusting plate 7. An arc-shaped shifting piece 8 is provided at a top of the sliding seat 6. A plurality of positioning slots 206 is provided inside the adjustment sliding groove 205, and the arc-shaped shifting piece 8 is fixedly sleeved in the positioning slot 206. The arc-shaped shifting piece 8 is provided on the top of the sliding seat 6. The two arc-shaped shifting pieces 8 are in a mirror-image structure. Each arc-shaped shifting piece is an arc-shaped plate with a certain degree of elasticity. The arc-shaped shifting piece 8 can be squeezed inward, allowing the sliding seat 6 to slide left or right inside the adjustment sliding groove 205, thereby positioning the sliding seat 6 at the fracture site. Then, according to the characteristics of the arc-shaped shifting piece 8, the arc-shaped shifting piece 8 may engage the positioning slots 206, securing the reduction arc plate 4 firmly in position.

Figure 6:
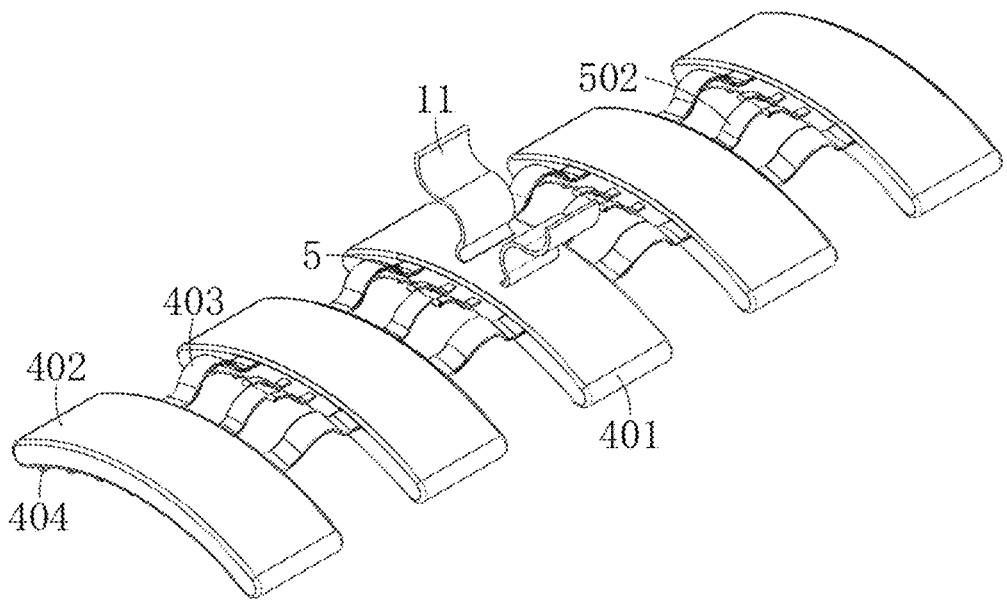
FIG. 6 is a schematic diagram of an enlarged three-dimensional structure of a reduction component from a first perspective.
Figure 7:
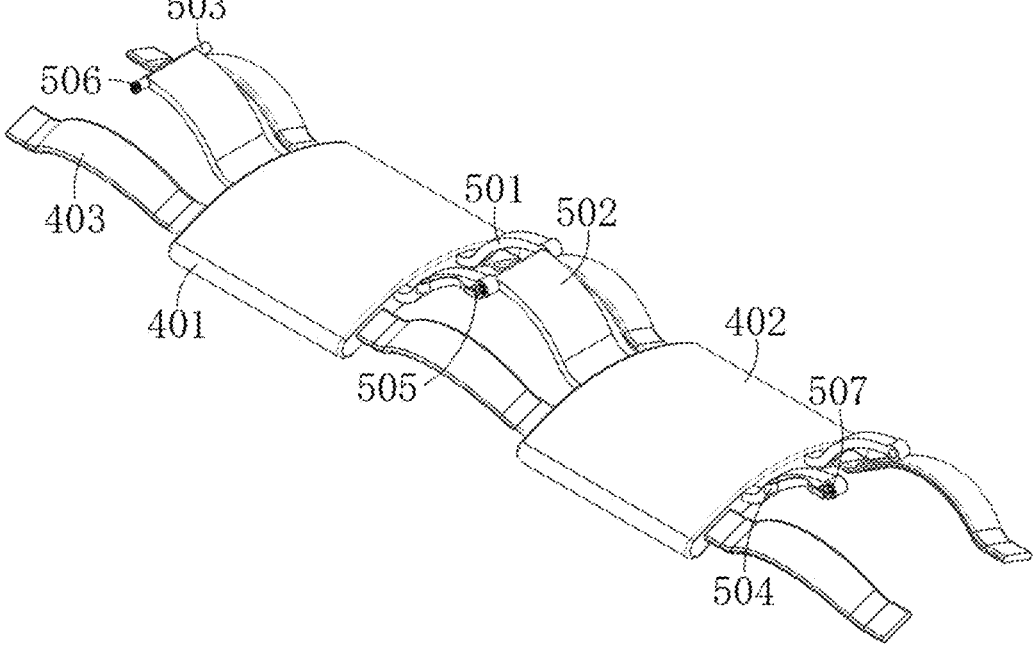
FIG. 7 is a schematic diagram of an enlarged three-dimensional structure of a reduction component from a second perspective.
Figure 8:
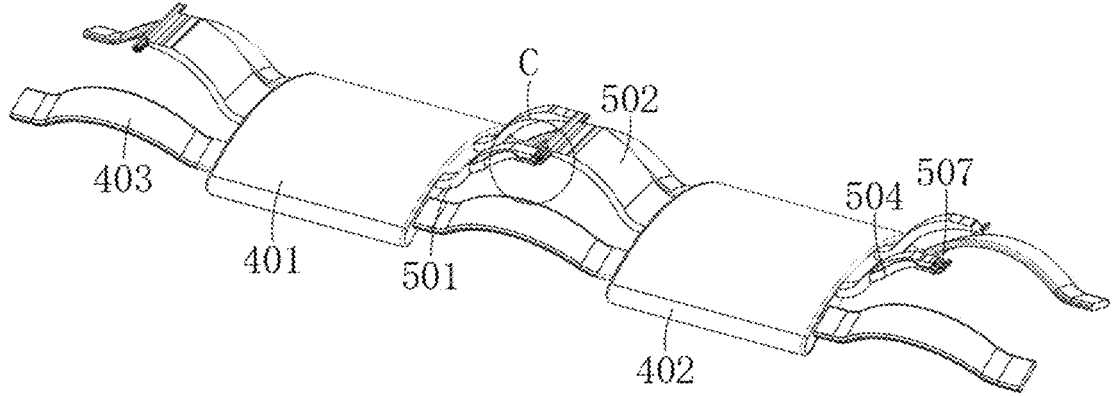
FIG. 8 is a schematic diagram of a cross-sectional three-dimensional structure of FIG. 7.
Figure 9:
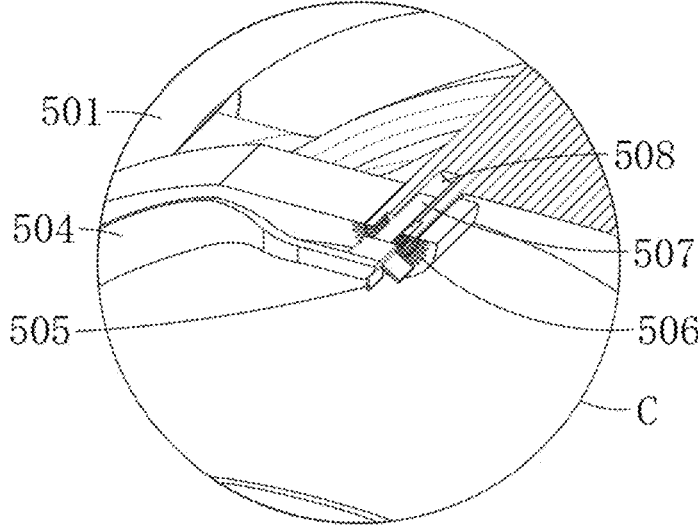
FIG. 9 is a schematic diagram of an enlarged three-dimensional structure of portion C in FIG. 8.

As shown in FIG. 5 and FIG. 6, a mounting clamp plate 11 is provided at the top of the reduction splint 401, and an outer wall of the adjusting plate 7 is provided with a mounting slot 21. The mounting clamp plate 11 is fixedly sleeved in the mounting slot 21. The mounting clamp plate 11 is arranged on the top of the reduction splint 401. The two mounting clamp plates 11 are in a mirror-image structure. Each mounting clamp plate 11 is an arc-shaped plate with a certain degree of elasticity. When it is necessary to mount the reduction arc plate 4 at the bottom of the adjusting plate 7, the reduction arc plate 4 can be directly sleeved inside the mounting slot 21 by virtue of the characteristics of the mounting clamp plate 11, thereby connecting the reduction arc plate 4 and the adjusting plate 7 together. This mounting method is simple and convenient.

Figure 2:
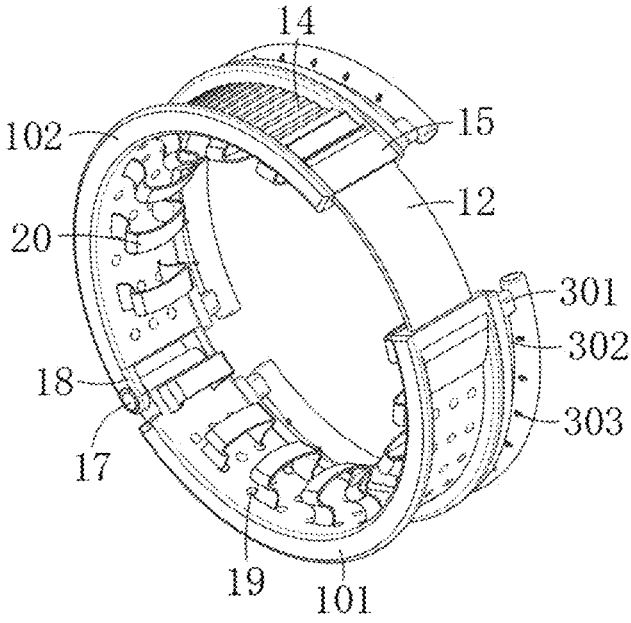
FIG. 2 is a schematic diagram of an enlarged three-dimensional structure of a fixed component.
Figure 3:
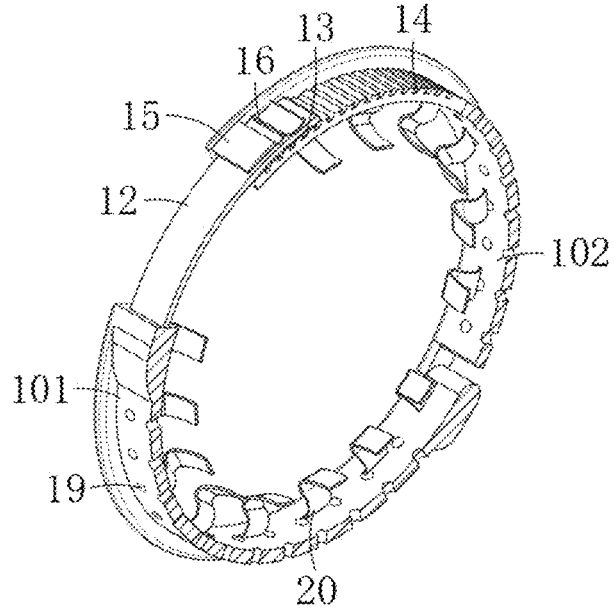
FIG. 3 is a schematic diagram of a cross-sectional three-dimensional structure of FIG. 2.

As shown in FIG. 2 and FIG. 3, an end of the first arc plate 101 is provided with a connecting plate 12, an inner wall of the connecting plate 12 is provided with a plurality of inserting blocks 13. A plurality of inserting slots 14 is provided inside the second arc plate 102, the inserting block 13 is fixedly sleeved in the inserting slot 14. A limiting baffle 15 is provided inside the second arc plate 102, and a sidewall of the limiting baffle 15 is provided with an elastic pressing plate 16. A further end of the first arc plate 101 is provided with a rotating shaft 17, and a further end of the second arc plate 102 is provided with a rotating frame 18. The rotating shaft 17 is rotatably sleeved in the rotating frame 18. A plurality of ventilation holes 19 is provided inside the first arc plate 101 and the second arc plate 102, and an inner wall of the first arc plate 101 and the second arc plate 102 is provided with a plurality of anti-slip elastic pieces 20. The C-shaped splint 1 is composed of the first arc plate 101 and the second arc plate 102. Both the first arc plate 101 and the second arc plate 102 are configured in a C-shaped open structure. This structure allows medical personnel to directly clamp the C-shaped splint 1 onto the patient's fractured part by means of its C-shaped open structure when mounting the splint onto the fractured site.

Furthermore, the connecting plate 12 and the corresponding limiting baffle 15 can be joined directly via the inserting block 13 and inserting slot 14, with the elastic pressing plate 16 pressing the inserting block 13 downward to lock them into the inserting slot 14. Since a plurality of inserting slots 14 is provided inside the second arc plate 102, medical personnel can selectively engage the inserting block 13 into the inserting slots 14 at different positions based on the size of the patient's fracture site, thereby increasing the application range of the C-shaped splint 1. The arrangement of the ventilation hole 19 on the C-shaped splint 1 not only improve overall breathability and comfort but also reduce the overall weight of the splint. Additionally, a plurality of anti-slip elastic pieces 20 is provided on the inner wall of the first arc plate 101 and the second arc plate 102. When the C-shaped splint 1 is installed on the patient's fractured part, the anti-slip elastic pieces 20 are squeezed and deformed, which enables the C-shaped splint 1 to be fixed on the fractured part and prevents the C-shaped splint 1 from sliding.

As shown in FIG. 6, an elastic plate 403 is provided between the reduction splint 401 and the movable splint 402. An inner wall of the reduction splint 401 and the movable splint 402 is provided with a plurality of anti-slip pads 404 made of rubber. The reduction arc plate 4 is an integrated structure composed of the reduction splint 401, the movable splint 402, and the elastic plate 403. The elastic plate 403 an arc-shaped plate with a certain degree of elasticity. The movable splint 402 is arranged linearly on both sides of the reduction splint 401 and connected to the reduction splint 401 via the elastic plate 403. The movable splints 402 are connected to each other via the elastic plate 403. Both the reduction splint 401 and the movable splint 402 are arc-shaped plates. When the reduction arc plate 4 is mounted onto the fracture site, the elastic plate 403 enables the movable splint 402 to conform closely to the curvature of the limb, meeting the clamping and fixing needs of different positions. Furthermore, the anti-slip pads 404 are provided on the inner walls of both the reduction splint 401 and the movable splint 402. When the reduction splint 401 and the movable splint 402 fit the curvature of the limb, the anti-slip pads 404 contact with the curvature of the limb, which can prevent the device from sliding during use.

The working principle of the technical solution provided by the present disclosure is as follows.

During use, two sets of C-shaped splints 1 are positioned on either side of the fixed splint 2. The fixed splint 2 is mounted onto the arc-shaped connecting frame 301 via the arc-shaped hook plate 202, assembling the two sets of C-shaped splints 1 into a unified structure. Then, the reduction arc plate 4 is attached to the bottom of the adjusting plate 7 using the mounting clamp plate 11. The C-shaped splint 1 is initially fitted onto the patient's uninjured limb. The position of the sliding seat 6 inside the adjustment sliding groove 205 is then adjusted according to the fracture location. The arc-shaped t shifting piece 8 secures the sliding seat 6 into the mounting slot 21. The adjusting screw 10, threaded into the threaded sleeve 9, brings the reduction splint 401 into contact with the limb surface. Under the action of the elastic plate 403, the movable splint 402 will conform to curvature of the limb, avoiding gaps between the reduction arc plate 4 and the limb which could cause secondary trauma to the fractured part during transport due to jostling. Then, under the action of the fixed pressing plate 504, the positioning clamping plate 505 is engaged within the positioning slot 506 inside the connecting frame 501 and connecting shaft 503, locking the angle between the connecting frame 501 and the connecting arc plate 502 as per the required fixation parameters. The device is then removed from the uninjured limb and mounted onto the fractured limb, allowing the inner surfaces of the reduction splint 401 and movable splint 402 to contact the limb. Finally, the first arc plate 101 and the second arc plate 102 are connected using the connecting plate 12. During this process, the reduction splint 401 and movable splint 402 can apply compressive force to rapidly realign the fracture and secure it in place.

The present disclosure encompasses all equivalents, modifications, and alternative methods or configurations falling within the spirit and scope of the present disclosure. To enable the public to have a thorough understanding of the present disclosure, preferred embodiments are described in detail above. However, for those skilled in the art, the present disclosure can also be fully understood without the description of these details. To avoid unnecessary confusion about the essence of the present disclosure, well-known methods, processes, procedures, components, and circuits are not elaborated here.

The above constitutes the preferred embodiments of the present disclosure. It should be noted that further improvements or modifications may be made by those skilled in the art without departing from the core principles of the present disclosure, and such variations are also considered within the protection scope of the present disclosure.

What is claimed is:

1. A device for rapid reduction and external fixation of a limb fracture, comprising:
   a C-shaped splint,
   a fixed splint,
   a reduction arc plate, and
   a limiting component, the C-shaped splint comprising a first arc plate and a second arc plate, a sidewall of the first arc plate and the second arc plate being provided with an arc-shaped connecting frame, the fixed splint being connected to the arc-shaped connecting frame, a sliding seat being slidably connected inside the fixed splint, a bottom of the sliding seat being provided with an adjusting plate, the reduction arc plate comprising a reduction splint and a movable splint, the reduction splint being arranged at a bottom of the adjusting plate, and the limiting component being arranged between the reduction splint and the movable splint;
   the limiting component comprising a connecting frame and a connecting arc plate, the connecting frame being arranged at an end of the reduction splint and movable splint, the connecting arc plate being arranged at a further end of the reduction splint and movable splint, an end of the connecting arc plate being provided with a connecting shaft, the connecting shaft being rotatably inserted into the connecting frame, an outer wall of the connecting frame being provided with a fixed pressing plate, a bottom of the fixed pressing plate being provided with a positioning clamping plate, a plurality of positioning slots being provided in the connecting frame and the connecting shaft, and the positioning clamping plate being fixedly sleeved in the plurality of positioning slots;
   wherein a limiting sliding groove is provided inside the connecting shaft, a limiting sliding rod is provided at a bottom of the positioning clamping plate, and the limiting sliding rod is slidably sleeved in the limiting sliding groove;
   wherein the fixed splint comprises an arc-shaped plate, both ends of the arc-shaped plate are provided with an arc-shaped hook plate, the arc-shaped connecting frame comprises an arc-shaped connecting bracket, the arc-shaped connecting bracket is provided on the sidewall of the first arc plate and the second arc plate, a hook groove matching a shape of the arc-shaped hook plate is formed between the arc-shaped connecting frame and the first arc plate, the arc-shaped hook plate is fixedly sleeved in the hook groove, an adjustment sliding groove is provided inside the arc-shaped plate, the sliding seat is slidably connected inside the adjustment sliding groove, and a mounting clamp plate is provided at a top of the reduction splint;
   wherein a threaded sleeve is provided inside the sliding seat, an adjusting screw is provided inside the threaded sleeve, a bottom of the adjusting screw is connected to a top of the adjusting plate, an outer wall of the adjusting plate is provided with a mounting slot, and the mounting clamp plate is fixedly sleeved in the mounting slot; and
   wherein an arc-shaped shifting piece is provided at a top of the sliding seat, a plurality of positioning slots is provided inside the adjustment sliding groove, and the arc-shaped shifting piece is fixedly sleeved in the positioning slot.

2. The device of claim 1, wherein an outer wall of the arc-shaped connecting frame is provided with a plurality of limiting blocks, a limiting slot is provided inside the arc-shaped hook plate, the limiting block is engaged inside the limiting slot, and an inner wall of the arc-shaped hook plate is provided with a weakening groove.

3. The device of claim 2, wherein an end of the first arc plate is provided with a connecting plate, an inner wall of the connecting plate is provided with a plurality of inserting blocks, a plurality of inserting slots is provided inside the second arc plate, the inserting block is fixedly sleeved in the inserting slot, a limiting baffle is provided inside the second arc plate, and a sidewall of the limiting baffle is provided with an elastic pressing plate.

4. The device of claim 1, wherein a further end of the first arc plate is provided with a rotating shaft, and a further end of the second arc plate is provided with a rotating frame, and the rotating shaft is rotatably sleeved in the rotating frame.

5. The device of claim 1, wherein a plurality of ventilation holes is provided inside the first arc plate and the second arc plate, and an inner wall of the first arc plate and the second arc plate is provided with a plurality of anti-slip elastic pieces.

6. The device of claim 1, wherein an elastic plate is provided between the reduction splint and the movable splint, an inner wall of the reduction splint and the movable splint is provided with a plurality of anti-slip pads, and the anti-slip pad is made of rubber.

\* \* \* \* \*